United States Patent [19]

Stetter et al.

[11] 4,267,338
[45] May 12, 1981

[54] N-AZOLYLALKYL-ANILINES

[75] Inventors: Jörg Stetter; Wilfried Draber; Rudolf Thomas; Winfried Lunkenheimer, all of Wuppertal, Fed. Rep. of Germany

[73] Assignee: Bayer Aktiengesellschaft, Leverkusen, Fed. Rep. of Germany

[21] Appl. No.: 10,784

[22] Filed: Feb. 9, 1979

[30] Foreign Application Priority Data

Feb. 10, 1978 [DE] Fed. Rep. of Germany ....... 2805756

[51] Int. Cl.$^3$ .................... A01N 43/82; C07D 271/10
[52] U.S. Cl. .................................... 548/143; 548/136; 548/138; 548/144; 548/263; 548/266; 71/88; 71/90
[58] Field of Search .................. 260/307 G; 548/143, 548/144, 136, 138, 266, 269, 263

[56] References Cited

U.S. PATENT DOCUMENTS 3,585,209  6/1971  Derappe .......................... 260/307 G

FOREIGN PATENT DOCUMENTS 2145513  3/1973  Fed. Rep. of Germany ........... 548/131
2625285  12/1976  Fed. Rep. of Germany ........... 548/143
1307283  2/1973  United Kingdom ..................... 548/144

OTHER PUBLICATIONS

Kraft et al., "Monatsh. Chem.", vol. 102, (1971), pp. 753–759.

Browne et al., "J. Hetero. Chem.", vol. 3, (1966), pp. 523–524.

Primary Examiner—Anton H. Sutto
Attorney, Agent, or Firm—Sprung, Felfe, Horn, Lynch & Kramer

[57] ABSTRACT

Novel N-azolylalkyl-aniline compound of the formula

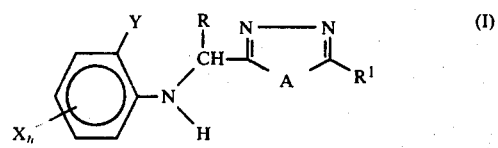

in which
A is oxygen, sulfur or the radical $>NR^2$,
R is hydrogen or alkyl,
$R^1$ is hydrogen, alkyl, haloalkyl, alkenyl, alkynyl, cycloalkyl, halogen, optionally substituted aryl, optionally substituted aralkyl or the radicals $-OR^3$, $-SR^3$ or $-NH^2R^3$,
$R^2$ is hydrogen, alkyl or optionally substituted aryl,
$R^3$ is hydrogen, alkyl, haloalkyl, alkenyl, alkynyl, cycloalkyl or optionally substituted aralkyl,
X is alkyl,
Y is alkyl or halogen and
n is 0, 1 or 2.

34 Claims, No Drawings

N-AZOLYLALKYL-ANILINES

The present invention relates to certain new N-azolylalkyl-aniline compounds. Such compounds are useful as intermediate products for the synthesis of herbicidal N-azolylalkylhalogenoacetanilides.

It is known that 2,6-diethyl-N-methoxymethyl-chloroacetanilide can be used for the selective combating of weeds (see R. Wegler, Chemie der Pflanzenschutz- und Schadlingsbekampfungsmittel (Chemistry of Plant Protection Agents and Agents for Combating Pests), volume 5, page 255, Springer-Verlag (1977)). However, this compound is not sufficiently active, especially against dicotyledons, and is not always completely satisfactory in its selectivity.

The present invention now provides, as new compounds, the N-azolyalkyl-anilines of the general formula

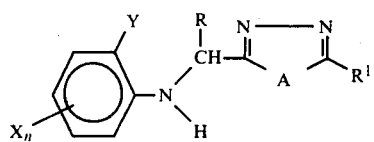

in which
A represents oxygen, sulphur or the grouping $>NR^2$,
R represents hydrogen or alkyl,
$R^1$ represents hydrogen, alkyl, halogenoalkyl, alkenyl, alkynyl, cycloalkyl, halogen, optionally substituted aryl, optionally substituted aralkyl or the grouping $-OR^3$, $-SR^3$ or $-NR^2R^3$,
$R^2$ represents hydrogen, alkyl or optionally substituted aryl,
$R^3$ represents hydrogen, alkyl, halogenoalkyl, alkenyl, alkynyl, cycloalkyl or optionally substituted aralkyl,
X represents alkyl,
Y represents alkyl or halogen and
n represents the number 0, 1 or 2.

The N-azolylalkyl-anilines of the formula (I) are suitable as intermediate products for the synthesis of N-azolylalkyl-halogenoacetanilides, which possess herbicidal properties.

Preferably, A represents oxygen, sulphur or the grouping $>NR^2$, wherein $R^2$ represents hydrogen, straight-chain or branched alkyl with 1 to 4 carbon atoms or aryl with 6 to 10 carbon atoms (especially phenyl), which may optionally carry one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine and chlorine);

R represents hydrogen or straight-chain or branched alkyl with 1 to 4 carbon atoms;

$R^1$ represents hydrogen, straight-chain or branched alkyl with 1 to 4 carbon atoms, halogenoalkyl with up to 3 carbon atoms and up to 5 identical or different halogen atoms (preferred halogens being fluorine and chlorine, and trifluoromethyl being mentioned as an example), alkenyl with 2 to 4 carbon atoms, alkynyl with 2 to 4 carbon atoms, cycloalkyl with 5 to 7 carbon atoms, halogen (especially fluorine, chlorine or bromine), aryl with 6 to 10 carbon atoms (especially phenyl) [the aryl radical optionally carrying one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine or chlorine, and trifluoromethyl being mentioned as an example)], aralkyl with 6 to 10 carbon atoms in the aryl part and 1 to 4 carbon atoms in the alkyl part (especially benzyl) [the aryl part of the aralkyl radical optionally carrying one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine or chlorine, and trifluoromethyl being mentioned as an example)] or the grouping $-OR^3$, $-SR^3$ or $-NR^2R^3$, wherein $R^2$ represents hydrogen, straight-chain or branched alkyl with 1 to 4 carbon atoms or aryl with 6 to 10 carbon atoms (especially phenyl), which may optionally carry one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine and chlorine) and $R^3$ represents hydrogen, straight-chain or branched alkyl with 1 to 4 carbon atoms, halogenoalkyl with up to 3 carbon atoms and up to 5 identical or different halogen atoms (preferred halogens being fluorine and chlorine, trifluoromethyl being mentioned as an example), alkenyl with 2 to 4 carbon atoms, alkynyl with 2 to 4 carbon atoms, cycloalkyl with 5 to 7 carbon atoms and aralkyl with 6 to 10 carbon atoms in the aryl part and 1 to 4 carbon atoms in the alkyl part (especially benzyl), the aryl part of the aralkyl radical optionally carrying one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine or chlorine, and trifluoromethyl being mentioned as an example);

X represents straight-chain or branched alkyl with 1 to 4 carbon atoms; and

Y represents straight-chain or branched alkyl with 1 to 4 carbon atoms, fluorine, chlorine or bromine.

The present invention also provides a process for the preparation of an N-azolylalkyl-aniline of the formula (I), in which (a) an aniline of the general formula

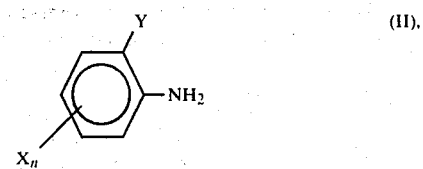

in which
X, Y and n have the meanings stated above,
is reacted with an azole derivative of the general formula

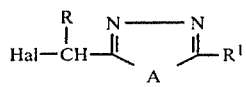

in which

A, R and R¹ have the meanings stated above and Hal represents chlorine or bromine, in the presence of an acid-binding agent and in the presence of a diluent, or (b) a hydrazine derivative of the general formula

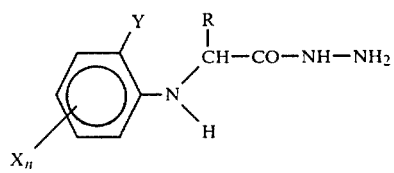

in which

R, X, Y and n have the meanings stated above,
is reacted with an isocyanate or isothiocyanate of the general formula

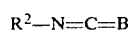 (V), in which

B represents oxygen or sulphur and
R² has the meaning stated above, in the presence of a diluent, the compound thereby formed, of the general formula

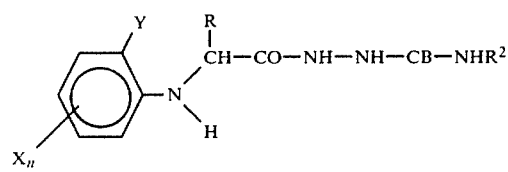

in which

B, R, R², X, Y and n have the meanings stated above,
is cyclized in the presence of a strong base and in the presence of a diluent, and the triazolone or triazolethione thereby formed, of the general formula

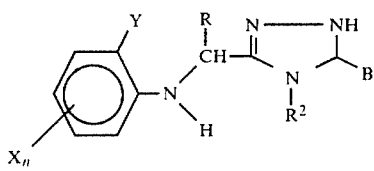

in which

B, R, R², X, Y and n have the meanings stated above,
is reacted with a halide of the general formula

 (VIII), in which

Hal represents chlorine or bromine and R⁴ represents alkyl, halogenoalkyl, alkenyl, alkynyl, or with another alkylating agent (i.e., other than that of the formula (VIII)), in the presence of a strong base and in the presence of a diluent and optionally in the presence of a phase transfer catalyst, or (c) a hydrazine derivative of the general formula (IV) is reacted with formic acid or with an acid chloride or acid anhydride, of the general formula

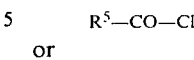 (IXa)

or

 (IXb)

in which

R⁵ represents alkyl, halogenoalkyl, alkenyl, alkynyl, cycloalkyl, optionally substituted aralkyl or optionally substituted aryl, in the presence of a diluent, and the compound thereby formed, of the formula

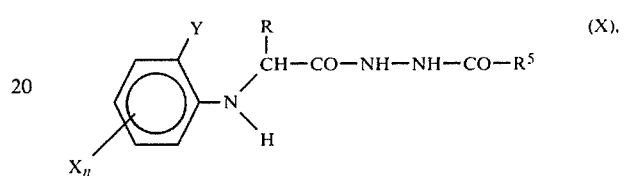

in which

R, R⁵, X, Y and n have the meanings stated above,
is either cyclized with diphosphorus pentasulphide in the presence of a diluent to give the thiadiazole derivative, or is reacted with an agent which splits off water, in the presence of a diluent, to give the oxadiazole derivative, or (d) a hydrazine derivative of the general formula (IV) is reacted with a nitrile of the general formula

 (XI), in which

R⁶ represents alkyl, halogenoalkyl or optionally substituted aryl, optionally in the presence of a diluent to give a triazole derivative, or (e) a hydrazine derivative of the formula (IV) is reacted with an imino-ether of the general formula

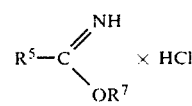

in which

R⁵ has the meaning stated above and
R⁷ represents methyl or ethyl, in the presence of a diluent to give an oxadiazole derivative, or (f) an aniline of the general formula (II) is reacted with an azole-aldehyde of the general formula

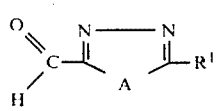

in which

R¹ and A have the meanings stated above,
in the presence of a diluent and the compound thereby formed, of the formula

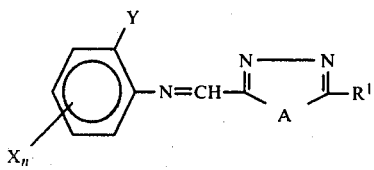

(XIV)

in which

A, R[1], X, Y and n have the meanings stated above, is reduced in the presence of a diluent.

Surprisingly, the N-azolylalkyl-halogenoacetanilides which can be prepared from the N-azolylalkyl-anilines of the formula (I) by reaction with halogenoacetic acid chlorides or anhydrides are considerably superior in their action against dicotyledons to the known compound 2,6-diethyl-N-methoxymethyl-chloroacetanilide, the action against monocotyledons being equivalent. Above all, however, they surprisingly exhibit a better selectivity in important cultivated plants than the above-mentioned, previously known compound, which is an active compound of the same type of action which has a high activity. As intermediate products for the synthesis of highly active herbicides, the compounds according to the invention thus represent a valuable enrichment of the art.

Specific examples of the compounds of the formula (I) are: 2,6-diethyl-N-(5-methyl-1,3,4-oxadiazol-2-yl-methyl)aniline, 2-ethyl-6-methyl-N-(5-methyl-1,3,4-oxadiazol-2-yl-methyl)-aniline, 2,6-dimethyl-N-(5-methyl-1,3,4-oxadiazol-2-yl-methyl)-aniline, 2-tert.-butyl-N-(5-methyl-1,3,4-oxadiazol-2-yl-methyl)-aniline, 2-chloro-6-tert.-butyl-N-(5-methyl-1,3,4-oxadiazol-2-yl-methyl)-aniline, 2-chloro-3-methyl-N-(5-methyl-1,3,4-oxadiazol-2-yl-methyl)-aniline, 2-chloro-5-methyl-N-(5-methyl-1,3,4-oxadiazol-2-yl-methyl)-aniline, 2-chloro-6-isopropyl-N-(5-methyl-1,3,4-oxadiazol-2-yl-methyl)-aniline, 2-isopropyl-N-(5-methyl-1,3,4-oxadiazol-2-yl-methyl)-aniline, 2-ethyl-6-isopropyl-N-(5-methyl-1,3,4-oxadiazol-2-yl-methyl)-aniline, 2-bromo-6-tert.-butyl-N-(5-methyl-1,3,4-oxadiazol-2-yl-methyl)-aniline, 2-bromo-6-isopropyl-N-(5-methyl-1,3,4-oxadiazol-2-yl-methyl)-aniline, 2,3-dimethyl-N-(5-methyl-1,3,4-oxadiazol)-2-yl-methyl)-aniline, 2,5-dimethyl-N-(5-methyl-1,3,4-oxadiazol-2-yl-methyl)-aniline, 2,6-diethyl-N-(5-ethyl-1,3,4-oxadiazol-2-yl-methyl)-aniline, 2-ethyl-6-methyl-N-(5-ethyl-1,3,4-oxadiazol-2-yl-methyl)-aniline, 2,6-dimethyl-N-(5-ethyl-1,3,4-oxadiazol-2-yl-methyl)-aniline, 2-tert.-butyl-N-(5-ethyl-1,3,4-oxadiazol-2-yl-methyl)-aniline, 2-chloro-6-tert.-butyl-N-(5-ethyl-1,3,4-oxadiazol-2-yl-methyl)-aniline, 2,6-diethyl-N-(5-isopropyl-1,3,4-oxadiazol-2-yl-methyl)-aniline, 2-ethyl-6-methyl-N-(5-isopropyl-1,3,4-oxadiazol-2-yl-methyl)-aniline, 2,6-dimethyl-N-(5-isopropyl-1,3,4-oxadiazol-2-yl-methyl)-aniline, 2-tert.-butyl-N-(5-isopropyl-1,3,4-oxadiazol-2-yl-methyl)-aniline, 2,6-diethyl-N-(5-n-propyl-1,3,4-oxadiazol-2-yl-methyl)-aniline, 2-ethyl-6-methyl-N-(5-n-propyl-1,3,4-oxadiazol-2-yl-methyl)-aniline, 2,6-dimethyl-N-(5-n-propyl-1,3,4-oxadiazol-2-yl-methyl)-aniline, 2-tert.-butyl-N-(5-n-propyl-1,3,4-oxadiazol-2-yl-methyl)-aniline, 2,6-diethyl-N-(5-phenyl-1,3,4-oxadiazol-2-yl-methyl)-aniline, 2,6-diethyl-N-(5-phenyl-1,3,4-oxadiazol-2-yl-methyl)-aniline, 2-ethyl-6-methyl-N-(5-trichloromethyl-1,3,4-oxadiazol-2-yl-methyl)-aniline, 2,6-dimethyl-N-(5-trichloromethyl-1,3,4-oxadiazol-2-yl-methyl)-aniline, 2-tert.-butyl-N-(5-trichloromethyl-1,3,4-oxadiazol-2-yl-methyl)-aniline, 2-chloro-6-tert.-butyl-N-(5-trichloromethyl-1,3,4-oxadiazol-2-yl-methyl)-aniline, 2,6-diethyl-N-(5-trifluoromethyl-1,3,4-oxadiazol-2-yl-methyl)-aniline, 2-ethyl-6-methyl-N-(5-trifluoromethyl-1,3,4-oxadiazol-2-yl-methyl)-aniline, 2,6-dimethyl-N-(5-trifluoromethyl-1,3,4-oxadiazol-2-yl-methyl)-aniline, 2-tert.-butyl-N-(5-trifluoromethyl-1,3,4-oxadiazol-2-yl-methyl)-aniline, 2-chloro-6-tert.-butyl-N-(5-trifluoromethyl-1,3,4-oxadiazol-2-yl-methyl)-aniline, 2,6-diethyl-N-(5-chloromethyl-1,3,4-oxadiazol-2-yl-methyl)-aniline, 2-ethyl-6-methyl-N-(5-chloromethyl-1,3,4-oxadiazol-2-yl-methyl)-aniline, 2,6-dimethyl-N-(5-chloromethyl-1,3,4-oxadiazol-2-yl-methyl)-aniline, 2,6-diethyl-N-(5-chloro-1,3,4-oxadiazol-2-yl-methyl)-aniline, 2-ethyl-6-methyl-N-(5-chloro-1,3,4-oxadiazol-2-yl-methyl)-aniline, 2,6-dimethyl-N-(5-chloro-1,3,4-oxadiazol-2-yl-methyl)-aniline, 2,6-diethyl-N-(5-bromo-1,3,4-oxadiazol-2-yl-methyl)-aniline, 2-ethyl-6-methyl-N-(5-bromo-1,3,4-oxadiazol-2-yl-methyl)-aniline, 2,6-diethyl-N-(5-methoxy-1,3,4-oxadiazol-2-yl-methyl)-aniline, 2-ethyl-6-methyl-N-(5-methoxy-1,3,4-oxadiazol-2-yl-methyl)-aniline, 2,6-dimethyl-N-(5-methoxy-1,3,4-oxadiazol-2-yl-methyl)-aniline, 2-tert.-butyl-N-(5-methoxy-1,3,4-oxadiazol-2-yl-methyl)-aniline, 2,6-diethyl-N-(5-methylthio-1,3,4-oxadiazol-2-yl-methyl)-aniline, 2-ethyl-6-methyl-N-(5-methylthio-1,3,4-oxadiazol-2-yl-methyl)-aniline, 2,6-dimethyl-N-(5-methylthio-1,3,4-oxadiazol-2-yl-methyl)-aniline, 2-tert.-butyl-N-(5-methylthio-1,3,4-oxadiazol-2-yl-methyl)-aniline, 2,6-diethyl-N-(5-dimethylamino-1,3,4-oxadiazol-2-yl-methyl)-aniline, 2-ethyl-6-methyl-N-(5-dimethylamino-1,3,4-oxadiazol-2-yl-methyl)-aniline, 2,6-dietheyl-N-(5-benzyl-1,3,4-oxadiazol-2-yl-methyl)-aniline, 2-ethyl-6-methyl-N-(5-benzyl-1,3,4-oxadiazol-2-yl-methyl)-aniline, 2,6-diethyl-N-(5-methyl-1,3,4-thiadiazol-2-yl-methyl)-aniline, 2-ethyl-6-methyl-N-(5-methyl-1,3,4-thiadiazol-2-yl-methyl)-aniline, 2,6-dimethyl-N-(5-methyl-1,3,4-thiadiazol-2-yl-methyl)-aniline, 2-tert.-butyl-N-(b 5-methyl-1,3,4-thiadiazol-2-yl-methyl)-aniline, 2-chloro-6-tert.-butyl-N-(5-methyl-1,3,4-thiadiazol-2-yl-methyl)-aniline, 2-chloro-3-methyl-N-(5-methyl-1,3,4-thiadiazol-2-yl-methyl)-aniline, 2-chloro-5-methyl-N-(5-methyl-1,3,4-thiadiazol-2-yl-methyl)-aniline, 2-chloro-6-isopropyl-N-(5-methyl-1,3,4-thiadiazol-2-yl-methyl)-aniline, 2-isopropyl-N-(5-methyl-1,3,4-thiadiazol-2-yl-methyl)-aniline, 2-ethyl-6-isopropyl-N-(5-methyl-1,3,4-thiadiazol-2-yl-methyl)-aniline, 2-bromo-6-tert.-butyl-N-(5-methyl-1,3,4-thiadiazol-2-yl-methyl)-aniline, 2-bromo-6-isopropyl-N-(5-methyl-1,3,4-thiadiazol-2-yl-methyl)-aniline, 2,3-dimethyl-N-(5-methyl-1,3,4-thiadiazol-2-yl-methyl)-aniline, 2,5-dimethyl-N-(5-methyl-1,3,4-thiadiazol-2-yl-methyl)-aniline, 2,6-diethyl-N-(5-ethyl-1,3,4-thiadiazol-2-yl-methyl)-aniline, 2-ethyl-6-methyl-N-(5-ethyl-1,3,4-thiadiazol-2-yl-methyl)-aniline, 2,6-dimethyl-N-(5-ethyl-1,3,4-thiadiazol-2-yl-methyl)-aniline, 2-tert.-butyl-N-(5-ethyl-1,3,4-thiadiazol-2-yl-methyl)-aniline, 2-chloro-6-tert.-butyl-N-(5-ethyl-1,3,4-thiadiazol-2-yl-methyl)-aniline, 2,6-diethyl-N-(5-isopropyl-1,3,4-thiadiazol-2-yl-methyl)-aniline, 2-ethyl-6-methyl-N-(5-isopropyl-1,3,4-thiadiazol-2-yl-methyl)-aniline, 2,6-dimethyl-N-(5-isopropyl-1,3,4-thiadiazol-2-yl-methyl)-aniline, 2-tert.-butyl-N-(5-isopropyl-1,3,4-thiadiazol-2-yl-methyl)-aniline, 2,6-diethyl-N-(5-n-propyl-1,3,4-thiadiazol-2-yl-methyl)-aniline, 2-ethyl-6-methyl-N-(5-n-propyl-1,3,4-thiadiazol-2-yl-methyl)-aniline, 2,6-dimethyl-N-(5-n-propyl-1,3,4-thiadiazol-2-yl-methyl)-aniline, 2-tert.-butyl-N-(5-n-propyl-1,3,4-thiadiazol- 2-yl-methyl)-aniline, 2,6-diethyl-N-(5-phenyl-1,3,4-thiadiazol-2-yl-methyl)-aniline, 2,6-diethyl-N-(5-phenyl-1,3,4-thiadiazol-2-yl-methyl)-aniline, 2-ethyl-6-methyl-N-(5-trichloromethyl-1,3,4-thiadiazol-2-yl-methyl)-aniline, 2,6-dimethyl-N-(5-trichloromethyl-1,3,4-thiadiazol-2-yl-methyl)-aniline, 2,6-dimethyl-N-(5-trichloromethyl-1,3,4-thiadiazol-2-yl-methyl)-aniline, 2-tert.-butyl-N-(5-trichloromethyl-1,3,4-thiadiazol-2-yl-methyl)-aniline, 2-chloro-6-tert.-butyl-N-(5-trichloromethyl-1,3,4-thiadiazol-2-yl-methyl)-aniline, 2,6-diethyl-N-(5-trifluoromethyl-1,3,4-thiadiazol-2-yl-methyl)-aniline, 2-ethyl-6-methyl-N-(5-trifluoromethyl-1,3,4-thiadiazol-2-yl-methyl)-aniline, 2,6-dimethyl-N-(5-trifluoromethyl-1,3,4-thiadiazol-2-yl-methyl)-aniline, 2-tert.-butyl-N-(5-trifluoromethyl-1,3,4-thiadiazol-2-yl-methyl)-aniline, 2-chloro-6-tert.-butyl-N-(5-trifluoromethyl-1,3,4-thiadiazol-2-yl-methyl)-aniline, 2,6-diethyl-N-(5-chloromethyl-1,3,4-thiadiazol-2-yl-methyl)-aniline, 2-ethyl-6-methyl-N-(5-chloromethyl-1,3,4-thiadiazol-2-yl-methyl)-aniline, 2,6-dimethyl-N-(5-chloromethyl-1,3,4-thiadiazol-2-yl-methyl)-aniline, 2,6-diethyl-N-(5-chloro-1,3,4-thiadiazol-2-yl-methyl)-aniline, 2-ethyl-6-methyl-N-(5-chloro-1,3,4-thiadiazol-2-yl-methyl)-aniline, 2,6-dimethyl-N-(5-chloro-1,3,4-thiadiazol-2-yl-methyl)-aniline, 2,6-diethyl-N-(5-bromo-1,3,4-thiadiazol-2-yl-methyl)-aniline, 2-ethyl-6-methyl-N-(5-bromo-1,3,4-thiadiazol-2-yl-methyl)-aniline, 2,6-diethyl-N-(5-methoxy-1,3,4-thiadiazol-2-yl-methyl)-aniline, 2-ethyl-6-methyl-N-(5-methoxy-1,3,4-thiadiazol-2-yl-methyl)-aniline, 2,6-dimethyl-N-(5-methoxy-1,3,4-thiadiazol-2-yl-methyl)-aniline, 2-tert.-butyl-N-(5-methoxy-1,3,4-thiadiazol-2-yl-methyl)-aniline, 2,6-diethyl-N-(5-methylthio-1,3,4-thiadiazol-2-yl-methyl)-aniline, 2-ethyl-6-methyl-N-(5-methylthio-1,3,4-thiadiazol-2-yl-methyl)-aniline, 2,6-dimethyl-N-(5-methylthio-1,3,4-thiadiazol-2-yl-methyl)-aniline, 2-tert.-butyl-N-(5-methylthio-1,3,4-thiadiazol-2-yl-methyl)-aniline, 2,6-diethyl-N-(5-dimethylamino-1,3,4-thiadiazol-2-yl-methyl)-aniline, 2-ethyl-6-methyl-N-(5-dimethylamino-1,3,4-thiadiazol-2-yl-methyl)-aniline, 2,6-diethyl-N-(5-benzyl-1,3,4-thiadiazol-2-yl-methyl)-aniline, 2-ethyl-6-methyl-N-(5-benzyl-1,3,4-thiadiazol-2-yl-methyl)-aniline, 2,6-diethyl-N-(5-ethylthio-1,3,4-thiadiazol-2-yl-methyl)-aniline, 2-ethyl-6-methyl-N-(5-ethylthio-1,3,4-thiadiazol-2-yl-methyl)-aniline, 2,6-dimethyl-N-(5-ethylthio-1,3,4-thiadiazol-2-yl-methyl)-aniline, 2-tert.-butyl-N-(5-ethylthio-1,3,4-thiadiazol-2-yl-methyl)-aniline, 2,6-diethyl-N-(5-allylthio-1,3,4-thiadiazol-2-yl-methyl)-aniline, 2-ethyl-6-methyl-N-(5-allylthio-1,3,4-thiadiazol-2-yl-methyl)-aniline, 2,6-dimethyl-N-(5-allylthio-1,3,4-thiadiazol-2-yl-methyl)-aniline, 2-tert.-butyl-N-(5-allylthio-1,3,4-thiadiazol-2-yl-methyl)-aniline, 2,6-diethyl-N-(5-benzylthio-1,3,4-thiadiazol-2-yl-methyl)-aniline, 2-ethyl-6-methyl-N-(5-benzylthio-1,3,4-thiadiazol-2-yl-methyl)-aniline, 2,6-dimethyl-N-(5-benzylthio-1,3,4-thiadiazol-2-yl-methyl)-aniline, 2-tert.-butyl-N-(5-benzylthio-1,3,4-thiadiazol-2-yl-methyl)-aniline, 2,6-diethyl-N-(5-isopropylthio-1,3,4-thiadiazol-2-yl-methyl)-aniline, 2-ethyl-6-methyl-N-(5-isopropylthio-1,3,4-thiadiazol-2-yl-methyl)-aniline, 2,6-dimethyl-N-(5-isopropylthio-1,3,4-thiadiazol-2-yl-methyl)-aniline, 2-tert-butyl-N-(5-isopropylthio-1,3,4-thiadiazol-2-yl-methyl)-aniline, 2,6-diethyl-N-(3,4-dimethyl-1,2,4-triazol-5-yl-methyl)-aniline, 2-ethyl-6-methyl-N-(3,4-dimethyl-1,2,4-triazol-5-yl-methyl)-aniline, 2,6-dimethyl-N-(3,4-dimethyl-1,2,4-triazol-5-yl-methyl)-aniline, 2-tert.-butyl-N-(3,4-dimethyl-1,2,4-triazol-5-yl-methyl)-aniline, 2,6-diethyl-N-(3-ethyl-4-methyl-1,2,4-triazol-5-yl-methyl)-aniline, 2-ethyl-6-methyl-N-(3-ethyl-4-methyl-1,2,4-triazol-5-yl-methyl)-aniline, 2,6-dimethyl-N-(3-ethyl-4-methyl-1,2,4-triazol-5-yl-methyl)-aniline, 2-tert.-butyl-N-(3-ethyl-4-methyl-1,2,4-triazol-5-yl-methyl)-aniline, 2,6-diethyl-N-(3-methyl-4-phenyl-1,2,4-triazol-5-yl-methyl)-aniline, 2-ethyl-6-methyl-N-(3-methyl-4-phenyl-1,2,4-triazol-5-yl-methyl)-aniline, 2,6-dimethyl-N-(3-methyl-4-phenyl-1,2,4-triazol-5-yl-methyl)-aniline, 2-tert.-butyl-N-(3-methyl-4-phenyl-1,2,4-triazol-5-yl-methyl)-aniline, 2,6-diethyl-N-(3-methylmercapto-4-methyl-1,2,4-triazol-5-yl-methyl)-aniline, 2-ethyl-6-methyl-N-(3-methylmercapto-4-methyl-1,2,4-triazol-5-yl-methyl)-aniline, 2,6-dimethyl-N-(3-methylmercapto-4-methyl-1,2,4-triazol-5-yl-methyl)-aniline, 2-tert.-butyl-N-(3-methylmercapto-4-methyl-1,2,4-triazol-5-yl-methyl)-aniline, 2,6-diethyl-N-(3-methoxy-4-methyl-1,2,4-triazol-5-yl-methyl)-aniline, 2-ethyl-6-methyl-N-(3-methoxy-4-methyl-1,2,4-triazol-5-yl-methyl)-aniline, 2,6-dimethyl-N-(3-methoxy-4-methyl-1,2,4-triazol-5-yl-methyl)-aniline, 2-tert.-butyl-N-(3-methoxy-4-methyl-1,2,4-triazol-5-yl-methyl)-aniline, 2,6-diethyl-N-(3-methyl-mercapto-4-phenyl-1,2,4-triazol-5-yl-methyl)-aniline, 2-ethyl-5-methyl-N-(3-methylmercapto-4-phenyl-1,2,4-triazol-5-yl-methyl)-aniline, 2,6-dimethyl-N-(3-methylmercapto-4-phenyl-1,2,4-triazol-5-yl-methyl)-aniline, 2-tert.-butyl-N-(3-methylmercapto-4-phenyl-1,2,4-triazol-5-yl-methyl)-aniline, 2,6-diethyl-N-(3-methoxy-4-phenyl-1,2,4-triazol-5-yl-methyl)-aniline, 2-ethyl-6-methyl-N-(3-methoxy-4-phenyl-1,2,4-triazol-5-yl-methyl)-aniline, 2,6-dimethyl-N-(3-methoxy-4-phenyl-1,2,4-triazol-5-yl-methyl)-aniline, 2-tert.-butyl-N-(3-methoxy-4-phenyl-1,2,4-triazol-5-yl-methyl)-aniline, 2,6-diisopropyl-N-(5-methyl-1,3,4-oxadiazol-2-yl-methyl)-aniline, 2,6-diethyl-N-(1,3,4-oxadiazol-2-yl-methyl)-aniline, 2,6-dimethyl-N-(1,3,4-oxadiazol-2-yl-methyl)-aniline, 2-ethyl-6-methyl-N-(1,3,4-oxadiazol-2-yl-methyl)-aniline, 2,6-diisopropyl-N-(1,3,4-oxadiazol-2-yl-methyl)-aniline, 2-tert.-butyl-N-(1,3,4-oxadiazol-2-yl-methyl)-aniline, 2-chloro-6-tert.-butyl-N-(1,3,4-oxadiazol-2-yl-methyl)-aniline, 2-bromo-6-tert.-butyl-N-(1,3,4-oxadiazol-2-yl-methyl)-aniline, 2,3-dimethyl-N-(1,3,4-oxadiazol-2-yl-methyl)-aniline, 2,5-dimethyl-N-(1,3,4-oxadiazol-2-yl-methyl)-aniline, 2-chloro-6-methyl-N-(1,3,4-oxadiazol-2-yl-methyl)-aniline, 2-chloro-6-ethyl-N-(1,3,4-oxadiazol-2-yl-methyl)-aniline, 2,6-diethyl-N-(1,3,4-thiadiazol-2-yl-methyl)-aniline, 2,6-dimethyl-N-(1,3,4-thiadiazol-2-yl-methyl)-aniline, 2,6-diisopropyl-N-(1,3,4-thiadiazol-2-yl-methyl)-aniline, 2-ethyl-6-methyl-N-(1,3,4-thiadiazol-2-yl-methyl)-aniline, 2-tert.-butyl-N-(1,3,4-thiadiazol-2-yl-methyl)-aniline, 2-chloro-6-methyl-N-(1,3,4-thiadiazol-2-yl-methyl)-aniline, 2,3-dimethyl-N-(1,3,4-thiadiazol-2-yl-methyl)-aniline, 2-chloro-6-tert.-butyl-N-(1,3,4-thiadiazol-2-yl-methyl)-aniline, 2,5-dimethyl-N-(1,3,4-thiadiazol-2-yl-methyl)-aniline, 2-bromo-6-tert.-butyl-N-(1,3,4-thiadiazol-2-yl-methyl)-aniline, 2,6-diisopropyl-N-(5-methyl-1,3,4-thiadiazol-2-yl-methyl)-aniline, 2,6-diethyl-N-(4-methyl-1,2,4-triazol-5-yl-methyl)-aniline, 2,6dimethyl-N-(4-methyl-1,2,4-triazol-5-yl-methyl)-aniline, 2,6-diisopropyl-N-(4-methyl-1,2,4-triazol-5-yl-methyl)-aniline, 2-tert.-butyl-N-(4-methyl-1,2,4-triazol-5-yl-methyl)aniline, 2-chloro-6-tert.-butyl-N-(4-methyl-1,2,4-triazol-5-yl-methyl)-aniline and 2-ethyl-6-methyl-(4-methyl-1,2,4-triazol-5-yl-methyl)-aniline.

If, for example, 2,6-diethylaniline and 2-chloromethyl-5-methyl-1,3,4-oxadiazole are used as starting materials, the course of the reaction in process variant (a) can be represented by the equation which follows:

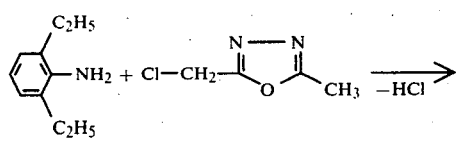

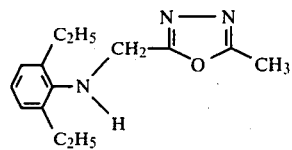

If, for example, 2,6-diethylanilino-acetic acid hydrazide and phenyl isothiocyanate are used as starting materials and dimethyl sulphate is used as an alkylating agent and triethyl-benzyl-ammonium chloride is used as a phase transfer catalyst, the course of process variant (b) can be represented by the equation which follows:

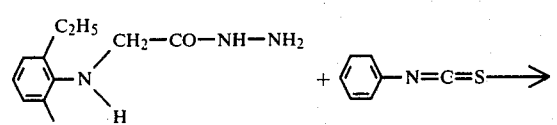

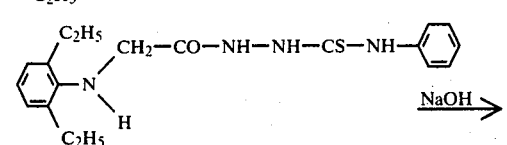

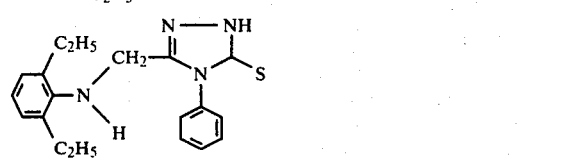

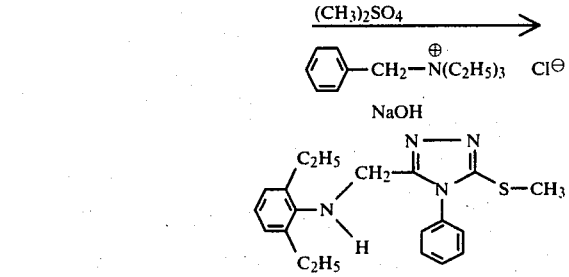

If, for example, 2-methyl-6-ethyl-anilino-acetic acid hydrazide and propionyl chloride are used as starting materials and diphosphorus pentasulphide is used as the cyclizing agent, the course of process variant (c) can be represented by the equation which follows:

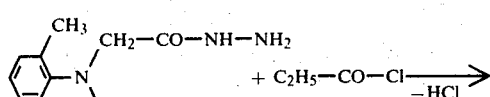

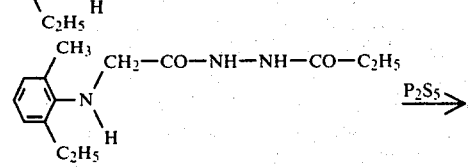

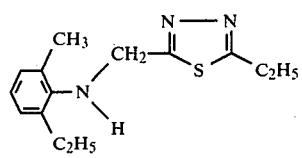

If, for example, 2,6-diethylanilino-acetic acid hydrazide and benzonitrile are used as starting materials, the course of process variant (d) can be represented by the equation which follows:

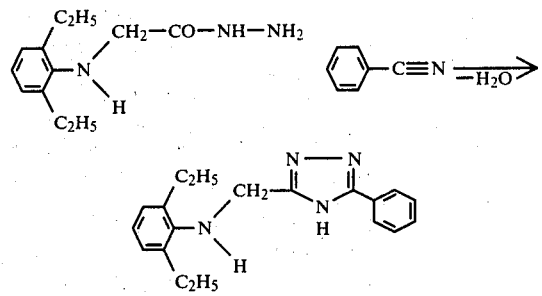

If, for example, 2,6-diethylanilino-acetic acid hydrazide and ethylimino-methyl-ether hydrochloride are used as starting materials, the course of process variant (e) can be represented by the equation which follows:

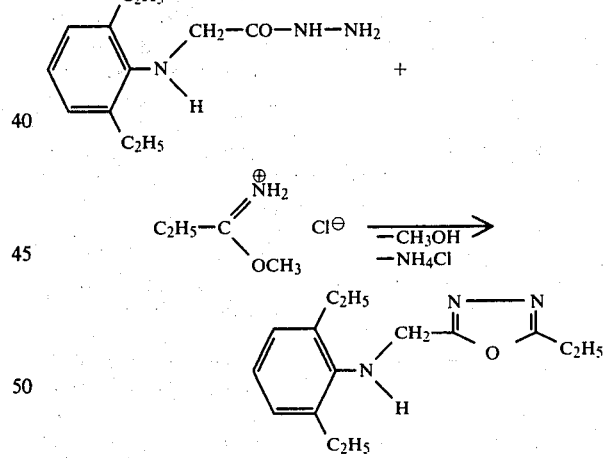

If, for example, 2,6-dimethylaniline and 2-formyl-1,3,4-thiadiazole are used as starting materials and sodium borohydride is used as the reducing agent, the course of process variant (f) can be represented by the equation which follows:

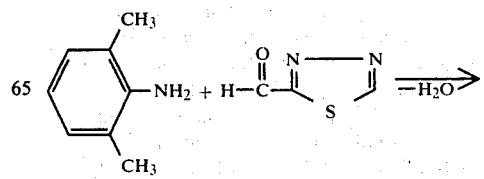

-continued

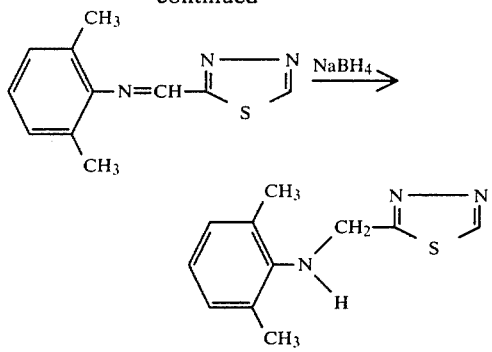

The compounds of the formula (II), to be used as starting materials in process variant (a) are known. Examples which may be mentioned are: 2-methylaniline, 2-ethylaniline, 2-propylaniline, 2-isopropylaniline, 2-butylaniline, 2-isobutylaniline, 2-sec.-butylaniline, 2-tert.-butylaniline, 2,6-dimethylaniline, 2,6-diethylaniline, 2-ethyl-6-methylaniline, 2,6-diisopropylaniline, 2,3-dimethylaniline, 2,4-dimethylaniline, 2,5-dimethylaniline, 2,6-dimethylaniline, 2-ethyl-3-methylaniline, 2-ethyl-4-meythylaniline, 2-ethyl-5-methylaniline, 2,4,6-trimethylaniline, 2,4,5-trimethylaniline, 2-ethyl-4,6-dimethylaniline, 2,6-diethyl-4-methylaniline, 2,6-diisopropyl-4-methylaniline, 2-chloro-6-methylaniline, 5-chloro-2-methylaniline, 3-chloro-2-methylaniline, 4-chloro-2-methylaniline and 2-chloro-6-tert.-butylaniline.

The formula (III) provides a general definition of the azole derivatives which additionally are required as starting materials in carrying out process (a) according to the invention. In this formula the radicals A, R and $R^1$ preferably have the meanings which have already been given for said radicals in connection with the preferred description of the compounds of the formula (I). The azole derivatives of the formula (III) are known, or they can be prepared by generally customary and known syntheses for heterocyclic compounds (see, in this context, inter alia, Helv. Chim. Acta 55, 1979 et seq. (1972); Chem. Ber. 32, 797 et seq. (1899) and 96, 1049 et seq. (1963)). Examples which may be mentioned are: 2-chloromethyl-5-methyl-1,3,4-oxadiazole, 2-chloromethyl-5-ethyl-1,3,4-oxadiazole, 2-chloromethyl-5-isopropyl-1,3,4-oxadiazole, 2-chloromethyl-5-trifluoromethyl-1,3,4-oxadiazole, 2-chloromethyl-5-trichloromethyl-1,3,4-oxadiazole, 2-chloromethyl-5-allyl-1,3,4-oxadiazole, 2-chloromethyl-5-cyclohexyl-1,3,4-oxadiazole, 2-chloromethyl-5-benzyl-1,3,4-oxadiazole, 2-chloromethyl-5-methoxy-1,3,4-oxadiazole, 2-chloromethyl-5-allyloxy-1,3,4-oxadiazole, 2-chloromethyl-5-(2-fluorobenzyloxy)-1,3,4-oxadiazole, 2-chloromethyl-5-methylthio-1,3,4-oxaidiazole, 2-chloromethyl-5-allylthio-1,3,4-oxadiazole, 2-chloromethyl-5-(2-fluorobenzylthio)-1,3,4-oxadiazole, 2-(1-chloroethyl)-5-methyl-1,3,4-oxadiazole, 2-(1-chloroethyl)-5-ethyl-1,3,4-oxadiazole, 2-chloromethyl-5-methyl-1,3,4-thiadiazole, 2-chloromethyl-5-ethyl-1,3,4-thiadiazole, 2-chloromethyl-5-isopropyl-1,3,4-thiadiazole, 2-chloromethyl-5-trifluoromethyl-1,3,4-thiadiazole, 2-chloromethyl-5-trichloromethyl-1,3,4-thiadiazole, 2-chloromethyl-5-allyl-1,3,4-thiadiazole, 2-chloromethyl-5-cyclohexyl-1,3,4-thiadiazole, 2-chloromethyl-5-benzyl-1,3,4-thiadiazole, 2-chloromethyl-5-methoxy-1,3,4-thiadizole, 2-chloromethyl-5-allyloxy-1,3,4-thiadiazole, 2-chloromethyl-5-(2-fluorobenzyloxy)-1,3,4-thiadiazole, 2-chloromethyl-5-methylthio-1,3,4-thiadiazole, 2-chloromethyl-5-allylthio-1,3,4-thiadiazole, 2-chloromethyl-5-(2-fluorobenzylthio)-1,3,4-thiadiazole, 2-(1-chloroethyl)-5-methyl-1,3,4-thiadiazole, 2-(1-chloroethyl)-5-ethyl-1,3,4-thiadiazole, 2-chloromethyl-5-methyl-1,3,4-triazole, 2-chloromethyl-5-ethyl-1,3,4-triazole, 2-chloromethyl-5-isopropyl-1,3,4-triazole, 2-chloromethyl-5-trifluoromethyl-1,3,4-triazole, 2-chloromethyl-5-trichloromethyl-1,3,4-triazole, 2-chloromethyl-5-allyl-1,3,4-triazole, 2-chloromethyl-5-cyclohexyl-1,3,4-triazole, 2-chloromethyl-5-benzyl-1,3,4-triazole, 2-chloromethyl-5-methoxy-1,3,4-triazole, 2-chloromethyl-5-allyloxy-1,3,4-triazole, 2-chloromethyl-5-(2-fluorobenzyloxy)-1,3,4-triazole, 2-chloromethyl-5-methylthio-1,3,4-triazole, 2-chloromethyl-5-allylthio-1,3,4-triazole, 2-chloromethyl-5-(2-fluorobenzylthio)-1,3,4-triazole, 2-(1-chloroethyl)-5-methyl-1,3,4-triazole, 2-(1-chloroethyl)-5-ethyl-1,3,4-triazole, 2-chloromethyl-1,5-dimethyl-1,3,4-triazole, 2-chloromethyl-5-ethyl-1-methyl-1,3,4-triazole, 2-chloromethyl-5-isopropyl-1-methyl-1,3,4-triazole, 2-chloromethyl-1-methyl-5-trifluoromethyl-1,3,4-triazole, 2-chloromethyl-1-methyl-5-trichloromethyl-1,3,4-triazole, 2-chloromethyl-5-allyl-1-methyl-1,3,4-triazole, 2-chloromethyl-5-cyclohexyl-1-methyl-1,3,4-triazole, 2-chloromethyl-5-benzyl-1-methyl-1,3,4-triazole, 2-chloromethyl-5-methoxy-1-methyl-1,3,4-triazole, 2-chloromethyl-5-allyloxy-1-methyl-1,3,4-triazole, 2-chloromethyl-5-(2-fluorobenzyloxy)-1-methyl-1,3,4-triazole, 2-chloromethyl-5-methylthio-1-methyl-1,3,4-triazole, 2-chloromethyl-5-allylthio-1-methyl-1,3,4-triazole, 2-chloromethyl-5-(2-fluorobenzylthio)-1-methyl-1,3,4-triazole, 2-(1-chloroethyl)-1,5-dimethyl-1,3,4-triazole and 2-(1-chloroethyl)-5-ethyl-1-methyl-1,3,4-triazole.

Any of the acid acceptors which can customarily be used may be employed as the acid-binding agent in carrrying out process variant (a), especially alkali metal carbonates, such as sodium carbonate or potassium carbonate.

Possible diluents for the reaction in process variant (a) are all the customary inert organic solvents, especially hydrocarbons, such as benzene, toluene and xylene, and polar solvents, such as dimethylformamide.

The reaction temperatures for process variant (a) can be varied within a substantial range. In general, the reaction is carried out at temperatures of from 20° C. to 160° C., preferably at from 60° C. to 120° C.

In carrying out process variant (a), 1 mole, or even a relatively large excess, of aniline of the formula (II) and 1 mole, or an excess, of acid-binding agent are preferably employed per mole of azole derivative of the formula (III). Isolation of the reaction products may be carried out by customary methods.

Examples which may be mentioned of hydrazine derivatives of the formula (IV), required as starting materials in carrying out process variant (b) are: 2,6-diethylanilino-acetic acid hydrazide, 2,6-dimethylanilinoacetic acid hydrazide, 2,4,6-trimethylanilino-acetic acid hydrazide, 2-ethyl-6-methylanilino-acetic acid hydrazide, α-(2,6-diethylanilino)-propionic acid hydrazide, α-(2,6-dimethylanilino-propionic acid hydrazide, α-(2,4,6-trimethylanilino)-propionic acid hydrazide and α-(2-ethyl-6-methylanilino-propionic acid hydrazide.

The hydrazine derivatives of the formula (IV) have not yet been described in the literature. However, they can be prepared by known processes, by reacting known esters (see, inter alia, DT-OS (German Published Specification) 2,350,944 and 2,513,730) of the general formula

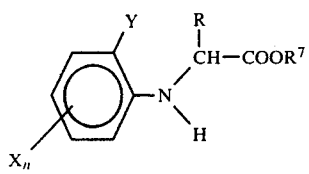

(XVI), in which

R, X, Y and n have the meanings stated above and R[7] represents methyl or ethyl, with hydrazine hydrate in the presence of an inert organic solvent, for example acetonitrile or dimethylformamide, at temperatures between 20° and 80° C. (see also the preparative Examples given later in this text).

The compounds of the formula (V), also required as starting materials in carrying out process variant (b), are known. Examples which may be mentioned are: methyl isothiocyanate, phenyl isocyanate, phenyl isothiocyanate, methyl isocyanate and ethyl isocyanate.

The compounds of the formula (VIII) required as reactants in carrying out process variant (b) are known. Examples which may be mentioned are: ethyl bromide, propyl bromide, phenyl bromide, cyclohexyl bromide and allyl bromide.

Instead of a halide of the formula (VIII) it is also possible to use other alkylating agents, for example dimethyl sulphate, and a phase transfer catalyst, for example triethyl-benzyl-ammonium chloride, in process variant (b).

A wide range of organic solvents can be used as the diluent for the reaction of the hydrazine derivative of the formula (IV) with the isocyanate or isothiocyanate of the formula (V) in carrying out process variant (b). Preferred solvents include alcohols, such as methanol or ethanol, and ethers, such as dioxan or tetrahydrofuran. Possible diluents for the subsequent cyclization of the compound of the formula (VI) initially formed are all the polar solvents, preferably alcohols, such as methanol or ethanol, and furthermore water. Possible diluents for the subsequent reaction of the triazolone or triazolethione of the formula (VII), formed by the cyclization, with the halide of the formula (VIII) or with another alkylating agent are all the inert organic solvents, especially hydrocarbons, such as benzene, toluene and xylene, and chlorinated hydrocarbons, such as methylene chloride and chloroform.

Possible bases both for the cyclization of the compounds of the formula (VI) and for the reaction of the triazolones or triazolethiones of the formula (VII) with halides of the formula (VIII) or with other alkylating agents are all the strong organic or inorganic bases, preferably the alkali metal hydroxides, such as sodium hydroxide or potassium hydroxide.

The reaction temperatures can be varied within a substantial range in carrying out process variant (b). The reaction of the hydrazine derivative of the formula (IV) with the isocyanate or isothiocyanate of the formula (V) is in general carried out at temperatures of from 0° C. to 80° C., preferably from 20° C. to 50° C. The cyclization of the compound of the formula (VI) is in general carried out at temperatures of from 20° C. to 100° C., preferably from 20° C. to 80° C. The reaction of the triazolone or triazolethione of the formula (VII) with the halide of the formula (VIII) or with another alkylating agent is in general carried out at temperatures of from 20° C. to 80° C., preferably from 20° C. to 60° C.

In carrying out process variant (b), 1 mole of isocyanate or isothiocyanate of the formula (V) is preferably employed per mole of hydrazine derivative of the formula (IV), the product of the formula (VI) thereby formed is then treated, after first isolating, with an equimolar amount, or with a slight excess, of a strong base and the triazolone or triazolethione of the formula (VII) thereby formed is isolated and reacted with an equimolar amount, or with a slight excess, of the halide of the formula (VIII) or another alkylating agent. Isolation of the reaction product is in each case carried out by customary methods.

The hydrazine derivatives of the formula (IV) that can be used as starting materials in carrying out process variant (c) have already been described in connection with the discussion of process variant (b).

The acid chlorides and acid anhydrides, of the formulae (IXa) and (IXb) respectively, are also required as starting materials in carrying out process variant (c). In the formulae (IXa) and (IXb) [and in formula (XII)], R[5] preferably represents straight-chain or branched alkyl with 1 to 4 carbon atoms, halogenoalkyl with up to 3 carbon atoms and up to 5 identical or different halogen atoms (especially fluorine and chlorine, trifluoromethyl being mentioned as an example), alkenyl or alkynyl with 2 to 4 carbon atoms, cycloalkyl with 5 to 7 carbon atoms, aryl with 6 to 10 carbon atoms or aralkyl with 6 to 10 carbon atoms in the aryl radical and 1 to 4 carbon atoms in the alkyl part (in particular benzyl), it being possible for each of these aryl radicals to be substituted by halogen, alkyl with 1 to 4 carbon atoms, alkoxy with 1 or 2 carbon atoms, alkylthio with 1 or 2 carbon atoms, cyano, nitro or halogenoalkyl with up to 2 carbon atoms and up to 5 identical or different halogen atoms (especially fluorine or chlorine, trifluoromethyl being mentioned as an example of halogenoalkyl).

The acid chlorides or acid anhydrides of the formulae (IXa) and (IXb) respectively are known, or they can be prepared by methods which are known in principle. Examples which may be mentioned are: acetyl chloride, propionyl chloride, benzoyl chloride, acetic anhydride and propionic anhydride.

The diphosphorus pentasulphide required as a reactant in carrying out process variant (c) is known.

Possible reagents which are capable of splitting off water from the compounds of the formula (XI) are all the customary dehydrating substances, preferably phosphorus pentoxide, polyphosphoric acid, sulphuric acid, thionyl chloride and phosphorus oxychloride, as well as zinc chloride.

Possible diluents for the reaction of the hydrazine derivative of the formula (IV) with the acid chloride or acid anhydride in process variant (c) are all the inert organic solvents, preferably methylene chloride, chloroform, dioxan, tetrahydrofuran, benzene and toluene.

Possible diluents for the subsequent cyclization of the initially formed compound of the formula (X) with diphosphorus pentasulphide or with an agent which splits off water are inert organic solvents. These include toluene, xylene, carbon tetrachloride or ethers, such as dioxan or tetrahydrofuran.

The reaction temperatures can be varied within a substantial range in carrying out process variant (c). The reaction of the hydrazine derivative of the formula (IV) with the acid chloride or acid anhydride of the formula (IXa) or (IXb) respectively is in general carried out at temperatures of from 0° C. to 50° C., preferably from 20° C. to 50° C. The cyclization of the compound of the formula (X) initially formed is in general carried out at temperatures of from 20° C. to 180° C., preferably from 60° C. to 150° C.

In carrying out process variant (c), 1 mole, or an excess, of an acid chloride or acid anhydride of the formula (IXa) or (IXb) respectively is preferably employed per mole of hydrazine derivative of the formula (IV) and the product of the formula (X) thereby formed is then isolated and reacted with diphosphorus pentasulphide or an agent suitable for splitting off water by methods which are known in principle (see Chem. Ber. 32, 797 (1899) and J. prakt. Chem. 69, 145 (1904) and Elderfield, Heterocyclic Compounds, volume 7, (1961)). Isolation of the reaction product is in each case carried out by customary methods.

Hydrazine derivatives of the formula (IV), to be used as starting materials in process variant (d), have already been described in connection with the discussion of process variant (b).

The nitriles of the formula (XI) are also required as starting materials in carrying out process variant (d). In this formula $R^6$ preferably represents alkyl with 1 to 4 carbon atoms, halogenoalkyl with 1 to 4 carbon atoms and 1 to 5 halogen atoms or represents aryl with 6 to 10 carbon atoms (in particular phenyl), which is optionally substituted by halogen, alkyl with 1 to 4 carbon atoms, halogenoalkyl with 1 to 4 carbon atoms and 1 to 5 halogen atoms, alkoxy with 1 to 4 carbon atoms or nitro.

The nitriles of the formula (XI) are known, or they can be prepared by methods which are known in principle. Examples which may be mentioned are: benzonitrile, acetonitrile, propionitrile and cyclohexylnitrile.

Possible diluents for process variant (d) are all the inert organic solvents, preferably toluene, xylene or dioxan.

The reaction can also be carried out in an autoclave under the autogenous pressure of the reactants, without a solvent.

The reaction temperatures for process variant (d) can be varied within a substantial range. In general, the reaction is carried out at temperatures of from 50° C. to 200° C., preferably from 120° C. to 200° C.

In carrying out process variant (d), 1 mole, or an excess, of nitrile of the formula (XI) is preferably employed per mole of hydrazine derivative of the formula (IV). (Compare Chem. Ber. 96, 1064 (1963).) Isolation of the reaction product is carried out by customary methods.

Hydrazine derivatives of the formula (IV), which have already been described in connection with the discussion of process variant (b), can also be used as starting materials in carrying out process variant (e).

The imino-ethers of the formula (XII) and their hydrochlorides, required as starting materials in process variant (e), are known, or they can be prepared by methods which are known in principle. Examples which may be mentioned are: acetimido acid methyl ester hydrochloride, benzimido acid ethyl ester hydrochloride and chloroacetimido acid ethyl ester hydrochloride.

Possible diluents for process variant (e) are all the polar organic solvents, preferably alcohols, such as methanol and ethanol.

The reaction temperatures for process variant (e) can be varied within a substantial range. In general, the reaction is carried out at temperatures of from 20° C. to 120° C., preferably from 50° C. to 80° C.

In carrying out process variant (e), 1 mole, or an excess, of imino-ether of the formula (XII), in the form of the appropriate hydrochloride, is preferably employed per mole of hydrazine derivative of the formula (IV). The mixture is worked up by customary methods.

Anilines of the formula (II) that can be used as starting materials in carrying out process variant (f) have already been described in connection with the discussion of process variant (a).

The azole-aldehydes of the formula (XIII) are also required as starting materials in carrying out process variant (f).

The azole-aldehydes of the formula (XIII) are known, or they can be prepared by methods which are known in principle (see Elderfield, Heterocyclic Compounds, volume 7 (1961) and Advances in Heterocyclic Chemistry, volume 9 (1968)).

Possible reducing agents for the reduction of the initially formed compounds of the formula (XIV) in carrying out process variant (f) are complex hydrides. Preferred are hydrides such as sodium borohydride.

Possible diluents for the reaction of the anilines of the formula (II) with azole-aldehydes of the formula (XIII) in process variant (f) are all the inert organic solvents, especially hydrocarbons, such as benzene, toluene and xylene. Possible diluents for the subsequent reduction of the compounds of the formula (XIV) initially formed are all the inert polar organic solvents, especially alcohols, such as methanol or ethanol.

The reaction temperatures can be varied within a substantial range in carrying out process variant (f). The reaction of the anilines of the formula (II) with azolealdehydes of the formula (XIII) is in general carried out at temperatures of from 80° C. to 120° C., preferably from 100° C. to 120° C. The subsequent reduction of the compounds of the formula (XIV) initially formed is carried out at from 0° C. to 50° C., preferably from 20° C. to 30° C.

In carrying out process variant (f), 1 mole, or an excess, of aniline of the formula (II) is preferably employed per mole of azole-aldehyde of the formula (XIII) and the product of the formula (XIV) thereby formed is then isolated and reduced with an excess of a hydrogen-releasing complex hydride. Isolation of the reaction products is in each case carried out by customary methods.

The N-azolylalkyl-anilines of the formula (I) are suitable as intermediate products for the synthesis of N-azolylalkyl-halogenoacetanilides, which possess herbicidal properties. The N-azolylalkyl-halogenoacetanilides of the general formula

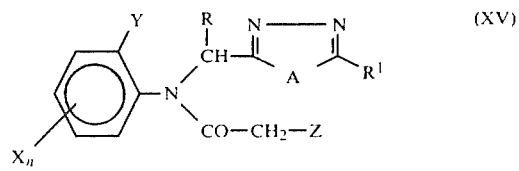

(XV)

in which
R, $R^1$, A, Y, X and n have the meanings stated above and
Z represents halogen.

can be prepared by reacting N-azolylalkylanilines of the formula

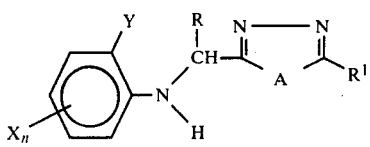

in which
R, $R^1$, A, X, Y and n have the meanings stated above, with halogenoacetic acid chlorides or anhydrides of the formula

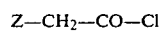

Z—CH$_2$—CO—Cl            (XVIa)

or (Z—CH$_2$—CO)$_2$O         (XVIb)

in which
Z has the meaning stated above, preferably chlorine, bromine or iodine,
in the presence of a diluent and optionally in the presence of an acid-binding agent.

The halogenacetic acid chlorides and anhydrides of the formulae (XVIa) and (XVIb) are generally known compounds of organic chemistry. Examples which may be mentioned are chloroacetyl chloride, bromoacetyl chloride and iodoacetyl chloride and the corresponding anhydrides.

Possible diluents for the reaction of the N-azolylalkyl-anilines according to the invention with halogenoacetic acid chlorides or anhydrides of the formulae (XVIa) and (XVIb) respectively are all the inert organic solvents, especially ketones, such as diethylketone, and in particular acetone and methyl ethyl ketone; nitriles, such as propionitrile, and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

The process indicated above for the preparation of N-azolylalkyl-halogenoacetanilides can optionally be carried out in the presence of acid-binding agents (hydrogen chloride-acceptors). All the customary acid-binding agents can be used as such agents, especially organic bases, such as tertiary amines, for example triethylamine, or such as pyridine; and furthermore inorganic bases, for example alkali metal hydroxides and alkali metal carbonates.

The reaction temperatures can be varied within a substantial range in carrying out the process indicated above for the preparation of N-azolylalkyl-halogenoacetanilides. In general, the reaction is carried out at from 0° to 120° C., preferably from 20° to 100° C.

In carrying out the process indicated above, 1 to 1.5 moles of halogenoacetylating agent and 1 to 1.5 moles of acid-binding agent are preferably employed per mole of the compound of the formula (I). Isolation of the compounds of the formula (XV) is carried out in the customary manner.

In addition to a good total herbicidal action, the N-azolylalkyl-halogenoacetanilides of the formula (XV) are distinguished, above all, by their possible selective uses in important cultivated plants, such as cotton, beet, rape and cereals. They are outstandingly suitable for pre-emergence use, but also show an action in the case of post-emergence use.

The good herbicidal actions of the N-azolylalkyl-halogenoacetanilides of the formula (XV) can be seen from the Example which follows.

ACTIVE COMPOUND LIST

The herbicidal action of the active compounds indicated below was tested in the Example which follows.

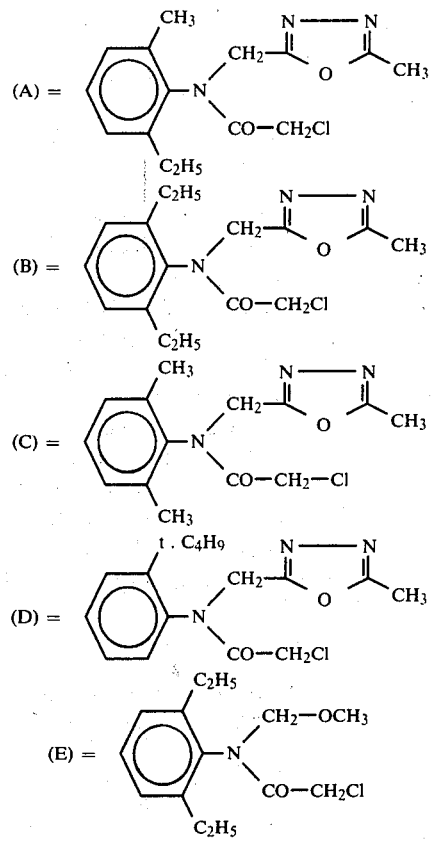

(Comparison compound)

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0%=no action (like untreated control)
100%=total destruction

In this test, the N-azolylalkyl-halogenoacetanilides of the formulae (A) to (D) showed a better selective herbicidal activity than the substance (E) known from the prior art.

PREPARATIVE EXAMPLES

EXAMPLE 1

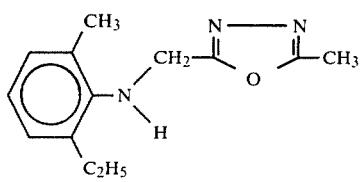
(1)

A mixture of 101.2 g (0.76 mol) of 2-ethyl-6-methylaniline, 40 g (0.3 mol) of 5-chloromethyl-1,3,4-oxadiazole, 41.4 g (0.3 mol) of powdered potassium carbonate and 76 ml of dimethylformamide was heated to 100° C. for 5 hours, while stirring. The reaction mixture was then filtered and the filtrate was diluted with methylene chloride and washed several times with water. The methylene chloride phase was dried over sodium sulphate and concentrated in vacuo by distilling off the solvent. The residue was distilled in vacuo. 46.8 g (67.5% of theory) of a yellowish oil consisting of 2-ethyl-6-methyl-N-[(2-methyl-1,3,4-oxadiazol-5-yl)-methyl]-aniline of boiling point 140°-142° C./0.1 mm Hg was obtained in a purity of 94% (determined by gas chromatography).

EXAMPLE 1a

Reaction of the compound (1) to give the corresponding N-azolylalkyl-halogenoacetanilide of the formula

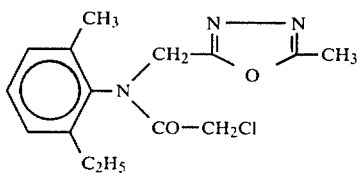
(1a)

16.3 g (0.07 mol) of 2-ethyl-6-methyl-N-[(2-methyl-1,3,4-oxadiazol-5-yl)-methyl]-aniline and 6 g (0.076 mol) of anhydrous pyridine were heated to the boil in 100 ml of absolute tetrahydrofuran, while stirring, and a solution of 8 g (0.07 mol) of chloroacetyl chloride in 20 ml of tetrahydrofuran was added dropwise. After the dropwise addition had ended, the mixture was stirred for a further 10 minutes and concentrated by distilling off the solvent and the residue was stirred with 150 ml of water. The reaction product which crystallized out was filtered off, washed with water and dried. 18.7 g (87% of theory) of beige-colored crystals of 2-ethyl-6-methyl-N-[(2-methyl-1,3,4-oxadiazol-5-yl)-methyl]-chloroacetanilide of melting point 67°-70° C. were obtained.

This compound is identified as test compound (A) in Example A.

EXAMPLE 2

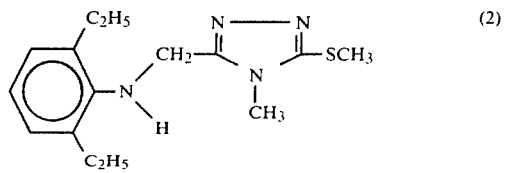
(2)

13.9 g (0.05 mol) of 2,6-diethyl-N-[(1-methyl-2-thiono-1,3,4-triazol-5-yl)-methyl]-aniline were stirred rapidly at room temperature in a two-phase mixture of 150 ml of toluene and 40 ml of 50% strength sodium hydroxide solution, 1.5 g of triethyl-benzyl-ammonium chloride (TEBA) being added as the catalyst, and 6.3 g (0.05 mol) of dimethyl sulphate were added dropwise, whereupon the temperature rose to about 35° C. The mixture was stirred for 5 hours and the toluene phase was separated off, washed several times with water, dried over sodium sulphate and concentrated by distilling off the solvent. The oil which remained was brought to crystallization by adding petroleum ether. After recrystallization from petroleum ether, 6.7 g (40% of theory) of 2,6-diethyl-N-[(1-methyl-2-methylthio-1,3,4-triazol-5-yl)-methyl]-aniline of melting point 65°-67° C. were obtained. Preparation of the precursors:

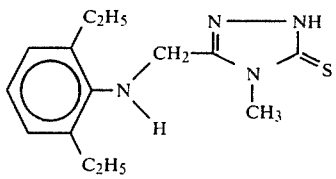

29.6 g (0.1 mol) of 1-methyl-4-[(2,6-diethyl-anilino)acetyl]-thiosemicarbazide were suspended in 150 ml of ethanol and, after adding 7 g of potassium hydroxide in 20 ml of water, the mixture was heated under reflux for 1 hour. Thereafter, most of the solvent was distilled off and 250 ml of water were added to the residue. After acidifying the mixture to pH 5 with glacial acetic acid, the precipitate formed was filtered off and washed thoroughly with water. After drying, 27 g (97% of theory) of 2,6-diethyl-N-[(1-methyl-2-thiono-1,3,4-triazol-5-yl)-methyl]-aniline of melting point 117°-121° C. were obtained.

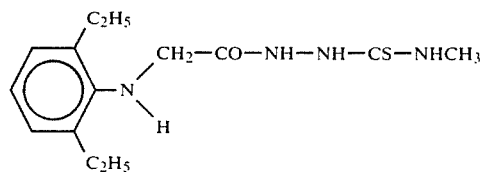

44.2 g (0.2 mol) of 2,6-diethyl-anilino-acetic acid hydrazide and 14.8 g (0.2 mol) of methyl isothiocyanate were dissolved in 250 ml of ethanol and the solution was heated to the reflux temperature for one hour. After subsequent cooling to room temperature, the precipitate formed was filtered off and rinsed twice with 50 ml of ethanol each time. After drying, 46 g (78% of theory) of 1-methyl-4-[(2,6-diethyl-anilino)-acetyl]-thiosemicarbazide were obtained in the form of a colorless crystalline substance of melting point 166° C.

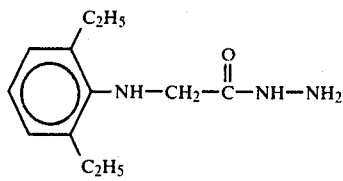

5

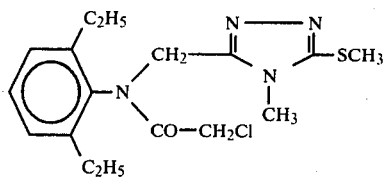

(2a)

58.7 g (0.25 mol) of 2,6-diethyl-anilino-acetic acid ethyl ester and 25 g of hydrazine hydrate were left to stand in 200 ml of ethanol for 24 hours. Thereafter, the mixture was concentrated by distilling off the solvent and the residue was extracted by stirring with water. After drying, 50.5 g (91% of theory) of colorless crystals of 2,6-diethyl-anilino-acetic acid hydrazide of melting point 71°–73° C. were obtained.

EXAMPLE 2a

Reaction of the compound (2) to give the corresponding N-azolylalkyl-halogenoacetanilide of the formula 5 g (0.017 mol) of 2,6-diethyl-N-[(1-methyl-2-methylthio-1,3,4-triazol-5-yl)-methyl]-aniline and 1.6 g (0.02 mol) of pyridine were stirred in 100 ml of absolute tetrahydrofuran, and 2.3 g (0.03 mol) of chloroacetyl chloride were added dropwise at room temperature, whereupon the temperature rose to about 30° C. The mixture was stirred for 2 hours and partly concentrated by distilling off the solvent, and water was added. The product which crystallized out was filtered off, dried and recrystallized from diisopropyl ether/ethyl acetate. 5 g (80% of theory) of 2,6-diethyl-N-[(1-methyl-2-methylthio-1,3,4-triazol-5-yl)-methyl]-chloroacetanilide of melting point 121°–123° C. were obtained.

Those compounds listed in Table 1 were obtained in a corresponding manner.

TABLE 1

| Example No. | R | $R^1$ | Y | $X_n$ | A | Melting point (°C.) or refractive index |
|---|---|---|---|---|---|---|
| 3 | H | $CH_3$ | $C_2H_5$ | 6-$C_2H_5$ | O | $n_D^{22}$ = 1.540 |
| 4 | H | $CH_3$ | $CH_3$ | 6-$CH_3$ | O | $n_D^{22}$ = 1.552 |
| 5 | H | $CH_3$ | t.-$C_4H_9$ | — | O | 52–55 |
| 6 | H | —S—$CH_2$—CH=$CH_2$ | $C_2H_5$ | 6-$C_2H_5$ | \N—$CH_3$/ | $n_D^{21}$ = 1.577 |
| 7 | H | —S—$CH_2$—(C$_6H_4$F) | $CH_3$ | 6-$C_2H_5$ | \N—$CH_3$/ | crude oil |
| 8 | H | $C_2H_5$ | $CH_3$ | 6-$C_2H_5$ | O | $n_D^{21}$ = 1.542 |
| 9 | H | $C_2H_5$ | $C_2H_5$ | 6-$C_2H_5$ | O | $n_D^{22}$ = 1.534 |
| 10 | H | i.-$C_3H_7$ | $CH_3$ | 6-$C_2H_5$ | O | $n_D^{21}$ = 1.531 |
| 11 | H | $CH_3$ | $CH_3$ | 3-$CH_3$ | \N—(2,3-di-$CH_3$-phenyl)/ | 142–143 |
| 12 | H | $CH_3$ | i-$C_3H_7$ | 6-i-$C_3H_7$ | O | 96–99 |

The compounds listed in Table 2 which follows were obtained from the compounds, according to the invention, of Examples 1 and 3 to 12, by reaction with chloroacetyl chloride or bromoacetyl chloride respectively.

TABLE 2

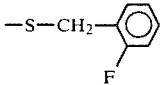

(XV)

| Example No. | R | R¹ | Y | $X_n$ | A | Z | Melting point (°C.) |
|---|---|---|---|---|---|---|---|
| 3 a | H | CH₃ | C₂H₅ | 6-C₂H₅ | O | Cl | 79–82 |
| 4 a | H | CH₃ | CH₃ | 6-CH₃ | O | Cl | 91–93 |
| 5 a | H | CH₃ | C(CH₃)₃ | — | O | Cl | 102–04 |
| 6 a | H | —S—CH₂—CH=CH₂ | C₂H₅ | 6-C₂H₅ | >N—CH₃ | Cl |  |
| 7 a | H | —S—CH₂—C₆H₄—F | CH₃ | 6-C₂H₅ | >N—CH₃ | Cl | 115–20 |
| 8 a | H | C₂H₅ | CH₃ | 6-C₂H₅ | O | Cl | 57–59 |
| 9 a | H | C₂H₅ | C₂H₅ | 6-C₂H₅ | O | Cl | 43–47 |
| 10 a | H | i-C₃H₇ | CH₃ | 6-C₂H₅ | O | Cl | viscous oil |
| 11 a | H | CH₃ | CH₃ | 3-CH₃ |  | Cl | glass-like solid |
| 12 a | H | CH₃ | C₂H₅ | 6-C₂H₅ | O | Br | 80 |
| 13 a | H | CH₃ | CH₃ | 6-C₂H₅ | O | Br | 92–94 |
| 14 a | H | CH₃ | i-C₃H₇ | 6-i-C₃H₇ | O | Cl | 135–137 |

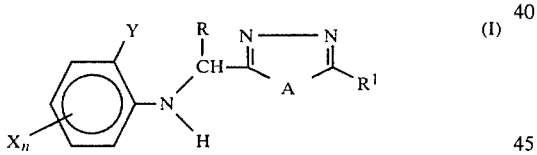

(for row 11a, A group: >N—C₆H₃(CH₃)₂)

It will be understood that the specification and examples are illustrative but not limitative of the present invention and that other embodiments within the spirit and scope of the invention will suggest themselves to those skilled in the art.

What is claimed is:

1. N-Azolylalkyl-aniline compound of the formula

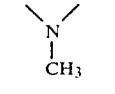

(I)

wherein A is oxygen, sulfur or $<NR^2$, wherein $R^2$ represents hydrogen, straight-chain or branched alkyl with 1 to 4 carbon atoms or aryl with 6 to 10 carbon atoms, which may optionally carry one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms;

R represents hydrogen or straight-chain or branched alkyl with 1 to 4 carbon atoms;

R¹ represents hydrogen, straight-chain or branched alkyl with 1 to 4 carbon atoms, halogenoalkyl with up to 3 carbon atoms and up to 5 identical or different halogen atoms, alkenyl with 2 to 4 carbon atoms, alkynyl with 2 to 4 carbon atoms, cycloalkyl with 5 to 7 carbon atoms, halogen, aryl with 6 to 10 carbon atoms, optionally carrying one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms; aralkyl with 6 to 10 carbon atoms in the aryl part and 1 to 4 carbon atoms in the alkyl part, optionally carrying one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms; or the grouping —OR³, —SR³ or —NR²R³, wherein R² represents hydrogen, straight-chain or branched alkyl with 1 to 4 carbon atoms or aryl with 6 to 10 carbon atoms, which may optionally carry one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms, and R³ represents hydrogen, straight-chain or branched alkyl with 1 to 4 carbon atms, halogenoalkyl with up to 3 carbon atoms and up to 5 identical or different halogen atoms, alkenyl with 2 to 4 carbon atoms, alkynyl with 2 to 4 carbon atoms, cycloalkyl with 5 to 7 carbon atoms and aralkyl with 6 to 10 carbon atoms in the aryl part and 1 to 4 carbon atoms in the alkyl part, the aryl part of the aralkyl radical optionally carrying one or more substituents selected independently from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms;

X represents straight-chain or branched alkyl with 1 to 4 carbon atoms;

Y represents straight-chain or branched alkyl with 1 to 4 carbon atms, fluorine, chlorine or bromine and n is 0, 1 or 2.

2. N-Azolylalkyl-aniline compound as claimed in claim 1 designated 2-ethyl-6-methyl-N-[(2-methyl-1,3,4-oxadiazol-5-yl)-methyl]-aniline.

3. N-Azolylalkyl-aniline compound as claimed in claim 3 designated 2-ethyl-6-methyl-N-[2-methyl-1,3,4-oxadiazol-5-yl)-methyl]-aniline.

4. N-Azolylalkyl-aniline compound as claimed in claim 1 designated 2,6-dimethyl-N-[2-methyl-1,3,4-oxadiazol-5-yl)-methyl]-aniline.

5. N-Azolylalkyl-aniline compound as claimed in claim 1 designated 2-tert.-butyl-N-[2-methyl-1,3,4-oxadiazol-5-yl)-methyl]-aniline.

6. N-Azolylalkyl-aniline compound as claimed in claim 1 designated 2-methyl-6-ethyl-N-[2-ethyl-1,3,4-oxadiazol-5-yl-methyl]-aniline.

7. N-Azolylalkylaniline compound as claimed in claim 1
$R^1$ is hydrogen, alkyl up to 4 carbon atoms, fluorine, chlorine or bromine —$OR^3$, —$SR^3$, or —$NR^2R^3$,
$R^2$ is hydrogen, alkyl of up to 4 carbon atoms or phenyl which may carry one or more substituents selected independently from halogen or alkyl with 1 to 4 carbon atoms
$R^3$ is hydrogen, alkyl of 1 to 4 carbon atoms, alkenyl with 2 to 4 carbon atoms, cycloalkyl with 5 to 7 ring carbon atoms or benzyl carrying one or more substituents selected independently from halogen and alkyl with 1 to 4 carbon atoms.

8. N-Azolylalkyl-aniline compound as claimed in claim 1 wherein A is oxygen.

9. N-Azolylalkyl-aniline compound as claimed in claim 1 wherein A is sulfur.

10. N-Azolylalkyl-aniline compound as claimed in claim 1 wherein A is >$NR^2$.

11. N-Azolylalkyl-aniline compound as claimed in claim 1 wherein R is hydrogen.

12. N-Azolylalkyl-aniline compound as claimed in claim 1 wherein R is alkyl of up to 4 carbon atoms.

13. N-Azolylalkyl-aniline compound as claimed in claim 1 wherein $R^1$ is hydrogen.

14. N-Azolyalkyl-aniline compound as claimed in claim 1 wherein $R^1$ is alkyl of up to 4 carbon atoms or halogenoalkyl of up to 3 carbon atoms.

15. N-Azolylalkyl-aniline compound as claimed in claim 1 wherein $R^1$ is alkenyl or alkynyl with 2 to 4 carbon atoms.

16. N-Azolylalkyl-aniline compound as claimed in claim 1 wherein $R^1$ is cycloalkyl with 5 to 7 ring carbon atoms.

17. N-Azolylalkyl-aniline compound as claimed in claim 1 wherein $R^1$ is optionally a substituted aryl or aralkyl of 6 to 10 carbon atoms in the aryl part and 1 to 4 carbon atoms in the alkyl part.

18. N-Azolylalkyl-aniline compound as claimed in claim 1 wherein $R^1$ is —$OR^3$.

19. N-Azolylalkyl-aniline compound as claimed in claim 1 wherein $R^1$ is —$SR^3$.

20. N-Azolylalkyl-aniline compound as claimed in claim 1 wherein $R^1$ is —$NR^2R^3$.

21. N-Azolylalkyl-aniline compound as claimed in claim 1 wherein $R^3$ is hydrogen.

22. N-Azolylalkyl-aniline compound as claimed in claim 1 wherein $R^3$ is alkyl or halogenoalkyl of up to 4 carbon atoms.

23. N-Azolylalkyl-aniline compound as claimed in claim 1 wherein $R^3$ is alkenyl or alkynyl.

24. N-Azolylalkyl-aniline compound as claimed in claim 1 wherein $R^3$ is cycloalkyl of 5 to 7 ring carbon atoms.

25. N-Azolylalkyl-aniline compound as claimed in claim 1 wherein $R^3$ is aryl or aralkyl of 6 to 10 carbon atoms in the aryl moiety and 1 to 4 carbon atoms in the alkyl moiety carrying one or more substituents selected independently from halogen, alkyl with 1 to 4 carbon atoms, alkylthio with 1 or 2 carbon atoms, cyano, nitro and haloalkyl with up to 2 carbon atoms and up to 5 halogen atoms.

26. N-Azolylalkyl-aniline compound as claimed in claim 1 wherein Y is halogen.

27. N-Azolylalkyl-aniline compound as claimed in claim 1 wherein n is 0.

28. N-Azolylalkyl-aniline compound as claimed in claim 1 wherein n is 1.

29. N-Azolylalkyl-aniline compound as claimed in claim 1 wherein n is 2.

30. N-Azolylalkyl-aniline compound as claimed in claim 7 wherein $R^1$ is halogen.

31. N-Azolylalkyl-aniline compound as claimed in claim 10 wherein A is $NH^2$.

32. N-Azolylalkyl-aniline compound as claimed in claim 10 wherein $R^2$ is alkyl of up to 4 carbon atoms.

33. N-Azolylalkyl-aniline compound as claimed in claim 10 wherein $R^2$ is optionally substituted aryl of 6 to 10 carbon atoms.

34. N-Azolylalkyl-aniline compound as claimed in claim 10 wherein Y is alkyl of up to 4 carbon atoms.

* * * * *

UNITED STATES PATENT AND TRADEMARK OFFICE
CERTIFICATE OF CORRECTION

PATENT NO. : 4,267,338
DATED : May 12, 1981
INVENTOR(S) : Jörg Stetter et al

It is certified that error appears in the above-identified patent and that said Letters Patent are hereby corrected as shown below:

Column 25, line 8, Delete "3" and insert --1--.

Signed and Sealed this

Tenth Day of November 1981

[SEAL]

Attest:

GERALD J. MOSSINGHOFF

Attesting Officer

Commissioner of Patents and Trademarks

Notice of Adverse Decision in Interference

In Interference No. 101,332, involving Patent No. 4,267,338, J. Stetter, W. Draber, R. Thomas and W. Lunkenheimer, N-AZOLYLALKYL-ANILINES, final judgment adverse to the patentees was rendered Oct. 7, 1985, as to claims 5, 15–20.

[*Official Gazette November 26, 1985.*]